US009784646B2

(12) United States Patent
Pan et al.

(10) Patent No.: US 9,784,646 B2
(45) Date of Patent: Oct. 10, 2017

(54) TREAD CRACKING INSPECTION DEVICE

(71) Applicants: Chinglin Pan, Mauldin, SC (US);
Ronald Cress, Simpsonville, SC (US);
Michael D. Petrovich, Simpsonville, SC (US)

(72) Inventors: Chinglin Pan, Mauldin, SC (US);
Ronald Cress, Simpsonville, SC (US);
Michael D. Petrovich, Simpsonville, SC (US)

(73) Assignee: Compagnie Générale des établissements Michelin, Clermont-Ferrand (FR)

( * ) Notice: Subject to any disclaimer, the term of this patent is extended or adjusted under 35 U.S.C. 154(b) by 118 days.

(21) Appl. No.: 14/764,886

(22) PCT Filed: Jan. 31, 2013

(86) PCT No.: PCT/US2013/024170
§ 371 (c)(1),
(2) Date: Jul. 30, 2015

(87) PCT Pub. No.: WO2014/120211
PCT Pub. Date: Aug. 7, 2014

(65) Prior Publication Data
US 2015/0369703 A1     Dec. 24, 2015

(51) Int. Cl.
*G01M 17/02* (2006.01)
*B65G 37/00* (2006.01)
(Continued)

(52) U.S. Cl.
CPC ......... *G01M 17/02* (2013.01); *B29D 30/0061* (2013.01); *B65G 37/00* (2013.01); *G01N 3/20* (2013.01); *B29D 2030/0066* (2013.01)

(58) Field of Classification Search
CPC ... G01M 17/02; B65G 37/00; B29D 30/0061; B29D 2030/0066; G01N 3/20
See application file for complete search history.

(56) References Cited

U.S. PATENT DOCUMENTS 1,954,483 A * 4/1934 Krall .................. G01N 3/20
                                                        73/812
2,281,476 A    4/1942 Casey
(Continued)

FOREIGN PATENT DOCUMENTS

FR    2433178 A1    3/1980
GB    1053641 A     1/1967
(Continued)

*Primary Examiner* — Blake A Tankersley
(74) *Attorney, Agent, or Firm* — Hahn Loeser & Parks LLP; Bret A. Hrivnak

(57) ABSTRACT

The present invention comprises methods and apparatus for inspecting a tread. Such methods include providing a tread having a top side and a bottom side, one of the top and bottom sides including a tread feature extending into the thickness of the tread. Such methods further include bending mechanically a transverse extent of the tread relative the tread thickness along a portion of the tread to be inspected about a bending member to form a bent portion of the tread, the portion of the tread to be inspected including the tread feature such that the step of bending expands the tread feature to further expose a depth of the tread feature within the thickness of the tread for inspection. Such further methods include constraining the tread on opposing sides of the portion of the tread to be inspected to maintain the bent portion of the tread in a bent arrangement.

22 Claims, 4 Drawing Sheets

(51) Int. Cl.
    *G01N 3/20*     (2006.01)
    *B29D 30/00*     (2006.01)

(56) References Cited

U.S. PATENT DOCUMENTS

| | | |
|---|---|---|
| 2,514,202 A | 7/1950 | Prettyman |
| 2,541,659 A | 2/1951 | McGovern |
| 4,160,537 A | 7/1979 | Severson |
| 4,184,664 A | 1/1980 | Ouriet et al. |
| 4,520,307 A | 5/1985 | Weiss et al. |
| 2012/0146262 A1 | 6/2012 | Adams et al. |

FOREIGN PATENT DOCUMENTS

| | | |
|---|---|---|
| GB | 1243666 A | 8/1971 |
| JP | H05-116235 A | 5/1993 |

\* cited by examiner

TREAD CRACKING INSPECTION DEVICE

This application is a National Stage application of International Application No. PCT/US2013/024170, filed Jan. 31, 2013.

BACKGROUND OF THE INVENTION

This invention relates generally to the inspection of tire treads, and more specifically, to the inspection of void features within the tread.

DESCRIPTION OF THE RELATED ART

It is known for treads, such as strips of tread for retreading tires, to include various tread features arranged along the top and/or bottom sides of the tread. These tread features may comprise, for example, grooves or sipes. Sipes are narrow grooves or even discontinuities, such as slices, extending into a thickness of the tread. When a tread is molded prior to application upon a tire carcass, such as, for example, during a retreading process, the pre-molded tread is demolded and subsequently inspected for the occurrence and severity of any defects or abnormalities. For example, cracks may occur along any tread feature as a result of the demolding process. During this inspection process, presently human operators bend a tread by hand to deflect the tread and thereby open particular tread features for the purpose of inspecting the full depth of the tread feature within a thickness of the tread. The problem is not only the physical effort exerted by the operator, but also the difficulties in trying to inspect the depth of the tread feature when both hands are being used to maintain the tread in a bent configuration. Accordingly, there is a need to improve the inspection of tread features arranged along a pre-molded tread.

SUMMARY OF THE INVENTION

The present invention provides methods and apparatus for inspecting a tread. In particular embodiments, the method includes providing a tread having a length, a width, and a thickness bounded by a top side and a bottom side, one of the top and bottom sides including a tread feature extending into the thickness of the tread. The embodiments of such methods further include bending mechanically a transverse extent of the tread relative the tread thickness along a portion of the tread to be inspected about a bending member to form a bent portion of the tread, the portion of the tread to be inspected including the tread feature such that the step of bending expands the tread feature to further expose a depth of the tread feature within the thickness of the tread for inspection. Finally, the embodiments of such methods include constraining the tread on opposing sides of the portion of the tread to be inspected to maintain the bent portion of the tread in a bent arrangement.

In particular embodiments, an apparatus for inspecting a tread includes a pathway configured to receive a tread. Such embodiments of the apparatus further include a bending member configured to engage a tread arranged along the pathway. Yet further, such embodiments of the apparatus include a first constraining member arranged along the pathway and a second constraining member arranged along the pathway, where the pathway extends lengthwise around a portion of the first member and around a portion of the bending member then around a portion of the third member, the bending member being arranged between the first and second members along the pathway.

The foregoing and other objects, features and advantages of the invention will be apparent from the following more detailed descriptions of particular embodiments of the invention, as illustrated in the accompanying drawings wherein like reference numbers represent like parts of the invention.

DETAILED DESCRIPTION OF PARTICULAR EMBODIMENTS

Figure 1:
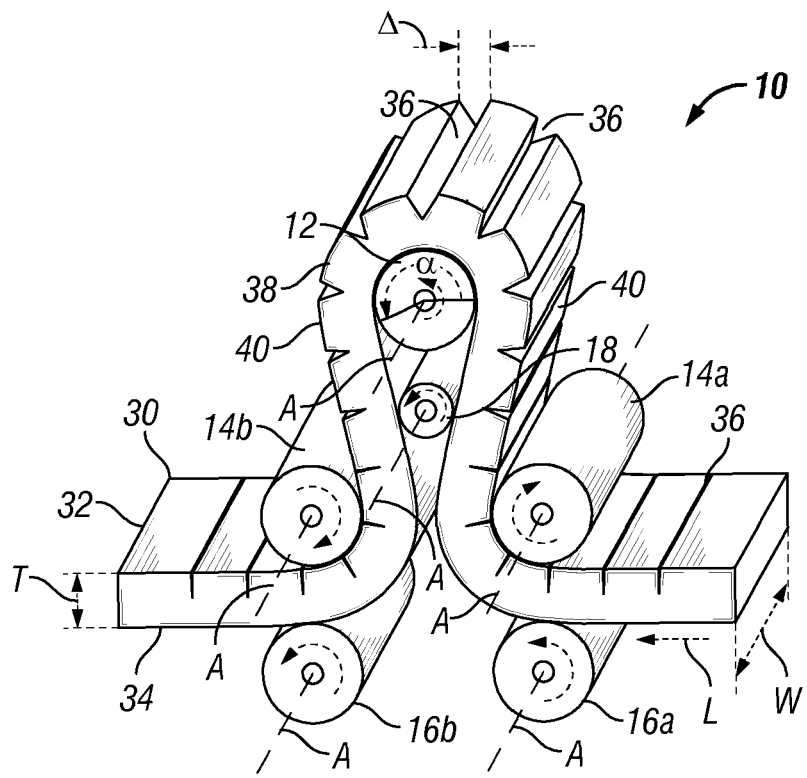
FIG. 1 is a side perspective view of a tread inspection device shown bending a tread along a bending member as well as along first and second members comprising first and second constraining members clamping a thickness of the tread at first and second locations and translating the tread through the device in accordance with an embodiment of the invention.

The present invention comprises methods and apparatus for inspecting tire treads. In particular embodiments, the inventive methods and apparatus are used to inspect pre-molded tire treads comprising a strip having a length defined by a first and a second end. Such treads are often employed in retread tire operations. Still, the inventive methods and apparatus may be employed to inspect any tread, including annular tread rings, and whether the tread is for a retreaded tire or an original tire.

The inventive methods and apparatus disclosed herein are used to improve the inspection of tire treads. In particular embodiments, a method of inspecting a tread includes the step of providing a tread having a length, a width, and a thickness bounded by a top side and a bottom side, one of the top and bottom sides including a tread feature extending into the thickness of the tread. In more specific embodiments, the tread comprises a strip having first and second ends arranged on opposite ends of the tread length. The tread elements comprise voids or discontinuities extending into a thickness of the tread. For example, tread elements may comprise grooves or sipes. Sipes are narrow grooves or even discontinuities, such as slits or slices, extending into a thickness of the tread. The top side of the tread is associated with a ground-engaging side of the tread along with a tire operates as it engages a ground surface. The bottom side is configured for attachment to a tire carcass, such as when forming a retreaded tire. The tread may be formed of any elastomeric material, including any natural or synthetic rubber, which may be vulcanized or cured with the application of heat.

Further embodiments of the methods may include the step of bending a transverse extent of the tread relative the tread thickness along a portion of the tread to be inspected about a bending member to form a bent portion of the tread, the portion of the tread to be inspected including the tread feature such that the step of bending expands the tread feature to further expose a depth of the tread feature within the thickness of the tread for inspection. To sufficiently inspect the depth of a tread feature, the tread feature must be sufficiently opened. In the present invention, this occurs by deforming the tread so to sufficiently expand the tread feature into an open configuration. This deformation and expansion of the tread feature is performed by bending the tread about a bending member. Accordingly, the tire tread is bent to open the tread feature for further inspection.

It is understood that the bending member may comprise any desired structure about which the tread is bent. In a particular embodiment, the bending member comprises one or more rollers, which means a single roller or a series of rollers having a common axis of rotation (where the axis of rotation of each roller is coaxial. It is understood, however, that the bending member may or may not rotate. It is also understood that the bending member may or may not be annular or have an annular outer surface. For example, the bending member may comprise a contoured sheet. It is also understood that any such roller may have a cylindrical out, tread-engaging surface, or may taper in diameter or otherwise vary from a cylindrical shape. In certain instances, the bending member may be sufficiently sized to extend fully or substantially across the full extent of the tread, while in other instances the bending member extends partially across the full extent of the tread.

In particular embodiments, bending the tread includes arranging the tread thickness to extend along a non-linear path extending between a first member and a second member and along the bending member located between the first and second constraining members along the path. Furthermore, the bent portion of the tread formed in the step of bending can be defined as having a bending radius extending from the side of the tread closest to the bending member. It is understood that the bending member may be formed to have any desired bending radius as needed to sufficiently open the tread feature to be inspected. When the bending member is an annular member, for example, the bending radius may comprise the outer radius of the bending member. In such instances, exemplary bending members may have an outer diameter of 25 to 65 mm, although it is understood that any other diameters may be employed as desired. If the diameter is too small, there is the possibility that the tread may crack. If the diameter is too large, the tread features will not sufficiently open and inspection thereof will not be achieved. It is appreciated that the bending member may not have an outer radius equal to the bending radius. For example, instances may arise where the tread separates from the bending member, such as when the bending member does not have an annular outer surface, resulting in a bending radius not equal to any outer radius or outer extent of the bending member.

In bending the tread along an axis extending perpendicular to the depthwise direction of the tread thickness, the tread may be bent along an axis extending in any direction perpendicular to the tread thickness. In particular embodiments, the tread is bent across an axis extending in a widthwise direction of the tread. It is also understood, however, that the bending axis can extend in a lengthwise direction of the tread or any direction between the widthwise and lengthwise directions.

In effect, the step of bending forms a bent portion of the tread to be inspected. The bend formed in the tread in the step of bending can be defined by an angle relative the rotational axis of the bending member, where the angle measures the angular distance along which the tread travels around the bending member. See angle $\alpha$ in FIG. 1, for example. It is understood that this final bent angle of the bent portion can be any angle desired to sufficiently open the tread feature to be inspected. For example, the angle may range between approximately 90 degrees and 200 degrees.

Because the tread feature is to be inspected, it is noted that the tread feature to be inspected is arranged along a side of the tread opposite the bending member relative the tread thickness. In other words, the tread feature is arranged opposite the side of the tread facing, closest to, or extending along the bending member. The side of the tread along which the tread feature is arranged is referred to as the exposed side of the tread, which is either the top or bottom side of the tread.

Particular embodiments of the methods include a step of constraining the tread on opposing sides of the portion of the tread to be inspected to maintain the bent portion of the tread in a bent arrangement. The step of constraining is performed to assist in the formation of the bent portion of the tread by maintaining the tread bent portion in a bent configuration. This may occur by arranging a first constraining member on a first side of the bent portion and a second constraining member on the second side of the bent portion to prevent each bent half of the bent portion from moving from its bent position. Accordingly, particular embodiments provide that the first member is a first constraining member and the second member is a second constraining member, the methods include constraining the thickness of the tread at a first location with the first constraining member and at a second location with the second constraining member prior to inspection. It is understood that additional constraining members may be used as necessary to properly secure the bent portion of the tread in a bent configuration. When referring to constraining members herein, unless otherwise noted, such reference refers to the first and second constraining members as well as any additional constraining member that may also be employed.

In performing the step of constraining, the constraining members may be freely movable while performing the step of constraining and maintaining the bent portion of the tread in the bent configuration. Nonetheless, in particular embodiments, a constraining member may generally prevent the tread from moving relative the constraining member while performing the step of constraining and maintaining the bent portion of the tread in the bent configuration. For example, a constraining member may include a projection or the like for insertion into any tread feature, such as a groove, to prevent substantial movement relative the constraining member. By further example, a constraining member may operate to clamp or pinch a thickness of the tread. Accordingly, in particular embodiments, each of the first and second constraining members are clamping members, and the step of constraining the thickness of the tread at a first location and a second location is accomplished by clamping.

Figure 5:
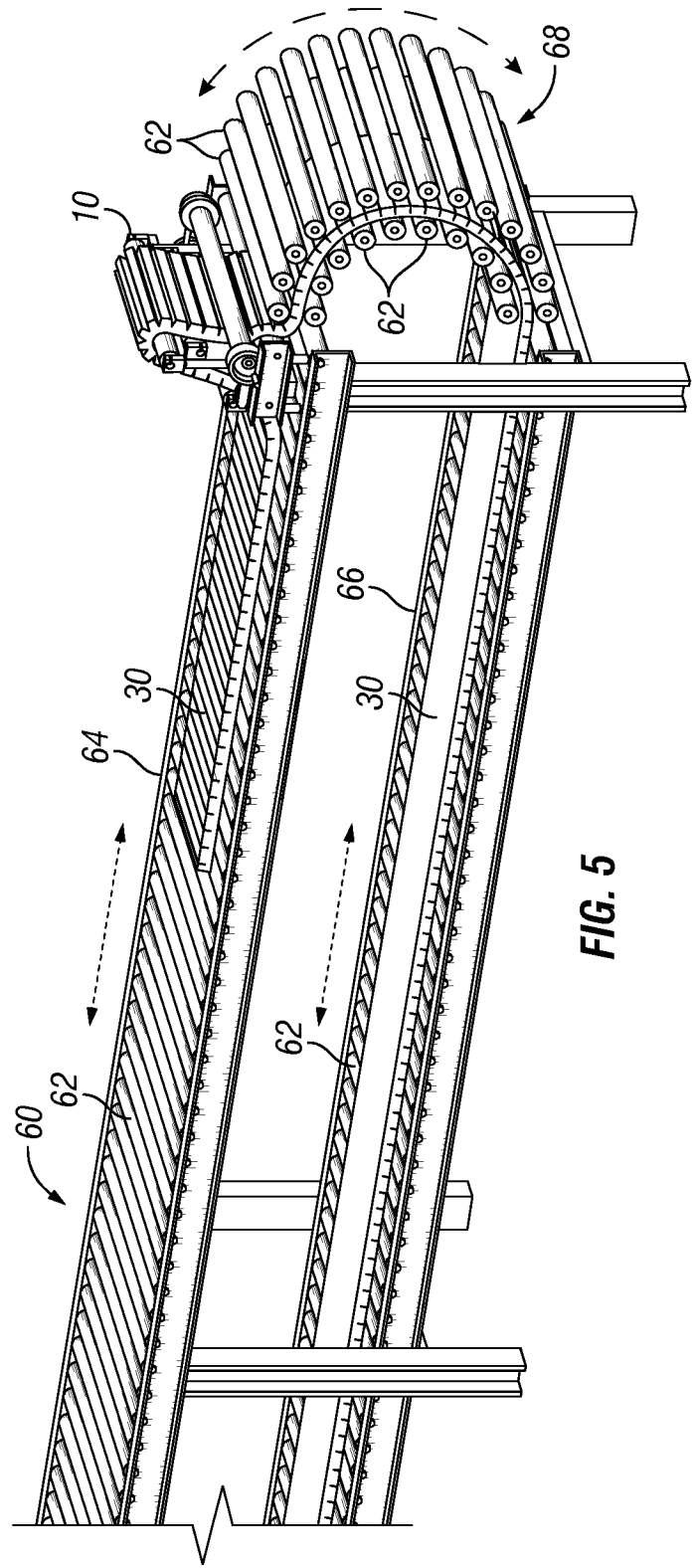
FIG. 5 is a perspective view of the tread inspection device of FIG. 4 shown attached to a tread support structure comprising a roller table and having a tread extending along top and bottom storage portions of the table in accordance with a further embodiment of the invention, although a portion of the tread is not shown to better show the inspection device.

It is appreciated that tread inspection may occur at any desired location. For example, tread inspection may occur while the tread is generally supported by a tread supporting structure. Moreover, the tread may be inspected as it is exiting the mold. Therefore, the bending member and the first and second members may be arranged in conjunction with or operably attached to any other structure at which the tread inspection is desired to occur. Therefore, in particular embodiments, the first constraining member operates in conjunction with a first opposing member arranged opposite the first constraining member relative the tread thickness to perform the step of constraining, and where the second constraining member operates in conjunction with a second opposing member arranged opposite the second constraining member relative the tread thickness to perform the step of constraining. It is understood that each of the first and second opposing members may comprise any desired structure. For example, each of the first and second opposing members may comprise a portion of a tread supporting structure, such as a table top or rollers arranged on a conveyor or table, which is exemplarily shown in FIG. 5. Therefore, in particular embodiments, each of the first and second constraining members operate in conjunction with a tread supporting structure to constrain the tread in the step of constraining, where the tread supporting structure supports portions of the tread separate from the portion being inspected. Furthermore, in further embodiments, the tread supporting structure includes a plurality of rotatable members each having a rotatable axis about which an outer surface of the rotatable member rotates to facilitate translation of the tread along the tread supporting structure, where a first rotatable member of the plurality of rotatable members operates in conjunction with the first constraining member to constrain the tread in the step of constraining and a second rotatable member of the plurality of rotatable members operates in conjunction with the second constraining member to constrain the tread in the step of constraining.

In particular embodiments, the step of constraining the tread occurs after the step of bending is performed to lock the tread in the bent configuration. It is understood, however, that the step of constraining may be performed prior to the step of bending, such as when the constrained portions of the tread translate with the tread as it moves inwardly as the bent portion of the tread is formed. This is further discussed below in association with FIG. 3.

It is understood that the tread can be released from constraint and the tread either removed or translated to a subsequent location along the tread for inspection. Accordingly, particular embodiments of such methods may further include the steps of releasing the tread from constraint as achieved in the step of constraining and translating the tread relative the bending member to a second portion of the tread to be inspected, the second portion of the tread including a second tread feature extending into the thickness of the tread from one of the top and bottom sides, and repeating the steps of bending and constraining in association with the second portion of the tread to be inspected. Of course, this may be repeated once or several times to inspect as many locations along the tread as desired.

Releasing the tread from constraint may be achieved by reversing the step of constraining. For example, if constraining is achieved by clamping or pinching the tread thickness, then releasing the tread from constraint would comprise removing the clamping or pinching force. In embodiments where constraint is achieved by simply positioning a constraining member in a location to resist any tendency of the bent portion to return to an un-deformed state by maintaining its location without applying any clamping or pinching force to a thickness of the tread, constraint of the tread may be released or removed by moving the constraint. It is understood that the tread may be transferred without removing the constraint, such as in the case of the later example, where, the tread may very easily be translated—even when the tread is under tension while the portion of the tread is being maintained in a bent configuration.

With regard to the step of translating, it is understood that the tread may be translated at one or more different speeds. For example, the tread may be selectively translated at a fast transfer speed so to quickly expel or remove the tread when inspection is complete, or to move quickly between different inspection locations. Furthermore, a mid-level speed may be selectively employed to translate the tread between closer inspection locations. A slow transfer speed may also be selectively employed to adjust the tread to more precisely configure the portion of the tread to be inspected along the bending member. Of course, additional speeds may be employed to transfer the tread as desired. Accordingly, in particular embodiments, the tread is translated in the step of translating at a first speed or a second speed, the first speed being faster than the second speed to perform a fast transfer of the tread between the each portion of the tread to be inspected.

Translation of the tread may be accomplished by any known means. For example, a driving force generated by any drive source, such as any motor or drive, may be operably communicated to the tread for translation. The driving force may be communicated by way of the bending member, any of the constraining members, and/or any other member arranged in communication with the tread. Furthermore, multiple drive sources may be employed to drive different members or the driving force from a single driving source may be distributed to more than one member by way of a connector, such as a belt, chain, gearing, rack and pinion, or the like.

Furthermore, during translation, the tread may remain engaged with the bending member, the first and second members, as well as any other constraining members and opposing members. Therefore, it is each such member may comprise a rotatable member having a rotatable axis about which an outer surface of the rotatable member rotates to engage the tread to facilitate translation of the tread relative each such member (that is any bending member, any constraining member, or opposing member as discussed herein). Of course, any one of such members may retract from engagement with the tread, regardless of whether any such member comprises a rotatable member. For example, in particular embodiments, the bending member is moveable in a direction toward the first and second members and in a direction away from the first and second members. The bending member may be moveable to reduce or increase the tension within the tread, to facilitate receipt of the tread within the network of members, and/or to form a non-linear path along which the tread extends between the first member, the bending member, and the second member.

It is also noted that the tread may slide along any such member having a fixed surface, meaning the surface does not rotate as the tread translates along the surface. Accordingly, any tread engaging surface of a fixed surface member (whether or not the member is a bending member, any constraining member or opposing member as discussed herein) may be a low-friction surface to facilitate sliding engagement of the tread during translation. Further, the outer, tread-engaging surface of any rotatable member may comprise a low friction surface or, if it is a driven rotatable member the tread engaging surface may include a high friction surface, at least in part, to promote the transfer of drive forces to the tread. A high friction surface may comprise any known high friction surface, and therefore may be texturized or even coated with any desired coating to increase or decrease friction between the tread and rotatable member.

It is appreciated that each of the bending member, the first and second bending members and any other constraining members and opposing members (as discussed herein) may comprise any longitudinal member, which may extend partially or fully across an extent of the tread to be bent. Furthermore, any or all of such members may extend longitudinally in parallel relation to each other. For example, when the first and second members are rotational members, the rotational axis of each of the first and second members are arranged in parallel. In further examples, when the bending member comprises a rotational member, the rotational axis of bending member is also parallel to the rotational axes of the first and second members.

Such methods will now be discussed in accordance with particular exemplary embodiments and in conjunction with the figures.

Figure 2:
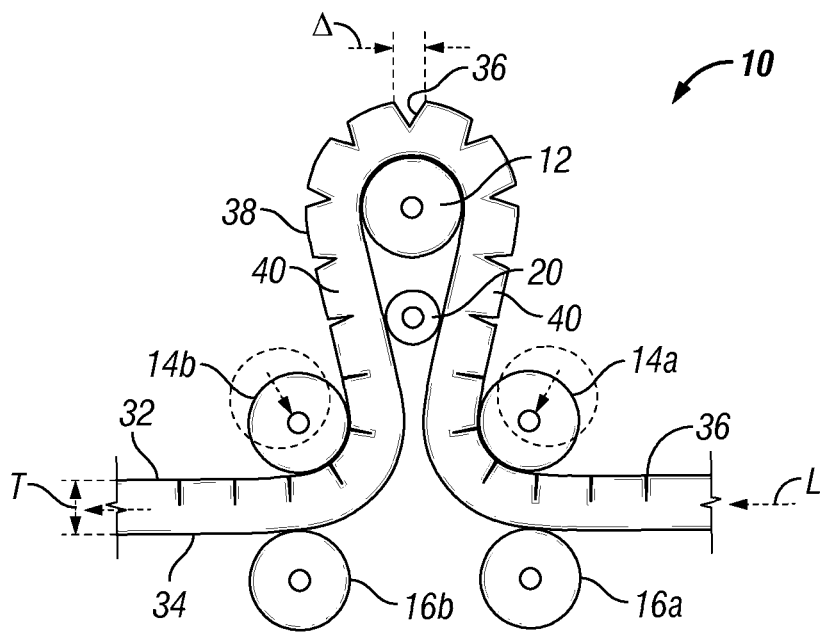
FIG. 2 is a side view of the tread inspection device of FIG. 1 showing a tread bent along a bending member as well as along first and second members comprising first and second constraining members where the constraining members are moveable in a direction away from opposing members and the tread in accordance with an embodiment of the invention.

With reference to FIGS. 1-2, an exemplary apparatus 10 is shown for inspecting a tread 30. The tread 30 is shown extending in a longitudinal direction L of the tread (that is, longitudinally) through a network of members comprising a bending member 12, a first member 14a, a second member 14b, a first opposing member 16a, and a second opposing member 16b. The network of members also includes a separating member 20 to maintain separation between opposing sides 40 of a bent portion 38 of the tread. The bent portion 38 comprises a portion of the tread to be inspected.

Each of the members shown are rotatable members, which form rollers in the embodiment shown. The rotational axes A of the members are all arranged in parallel, and each of the rotatable members have a cylindrical outer surface 20. The rotatable members extend across the full transverse extent of the tread, which, in the embodiment shown, comprises a width W of the tread. The thickness T is defined by a top side 32 and a bottom side 34 of the tread. The tread 30 further includes tread features 36 comprising sipes arranged along the top side 32 of the tread and within the bent portion 38. The sipes 36 are shown to deflect openly, or, in other words, expand as represented by A when arranged about the bending member 12 and within bent portion 38.

It is also noted that tread 30 follows a non-linear path defining a pathway 42 through the network of members, the pathway being configured to receive the tread. Accordingly, it can be said that each of the bending member 12 as well as the first and second constraining members 14a, 14b and the opposing members 16a, 16b are arranged along the pathway and are configured to engage a tread arranged along the pathway 42. It can also be said that the pathway 42 extends lengthwise around a portion of the first member 14a and around a portion of the bending member 12 then around a portion of the second member 14b, the bending member being arranged between the first and second members along the pathway With particular regard to the bent portion 38 of the tread, it is shown that the tread extends about the bending member 12 by angle $\alpha$. In particular embodiments, the angle $\alpha$ is at least 90 degrees, while in other variations, angle $\alpha$ is at least equal to 135 degrees or 180 degrees. In the embodiment shown, angle $\alpha$ is greater than 180 degrees.

Figure 3:
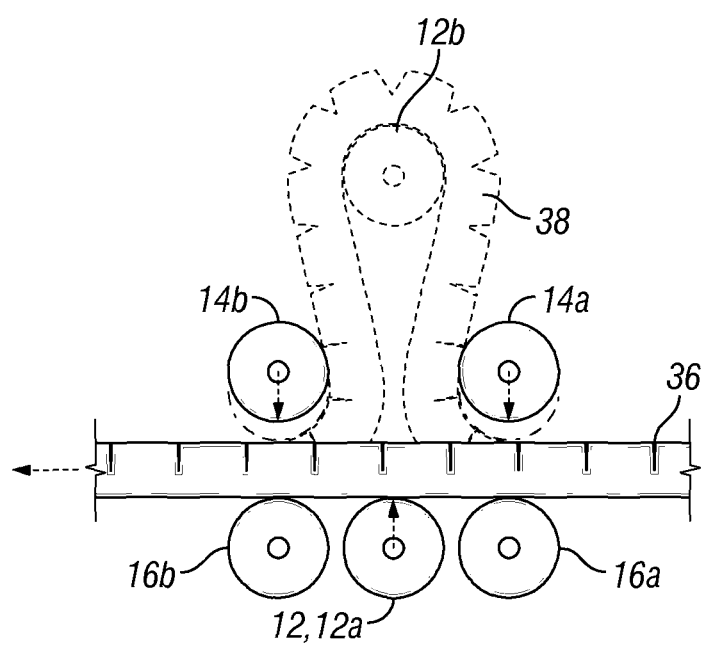
FIG. 3 is a side view of a tread inspection device in accordance with an alternative embodiment of the invention showing the bending member being displaceable such that the tread is able to translate through the apparatus without being bent about a portion of the bending member as the bending member is in a retracted arrangement between the first and second members.

With particular reference to FIG. 3, an embodiment of the invention is shown where the bending member 12 is moveable between a retracted position 12a and a tread-engaging position 12b. This allows the bending member 12 to adjust the tension within tread 30, and to further deflect any tread feature 36 for inspection. Furthermore, in particular embodiments the bending member 12 may be able to move sufficiently from its tread-engaging position, such as is shown in the FIG. 3 by example, to better facilitate translation of the tread through the inspection device, and to even facilitate the ability of the tread to translate at higher speeds. Moreover, by sufficiently moving the bending member 12 below any tread supporting structure, which is also represented by first and second opposing members 16a, 16b in the embodiment shown in FIG. 3, the tread 30 may more easily be inserted into the inspection device 10 and configured into a bent configuration 38 mechanically or automatically without or with reduced manual assistance by an operator. Additionally, it is shown that first and second constraining members 14a, 14b move or translate towards and away from the tread 30 to selectively constrain and release the tread as necessary in performing the methods disclosed herein.

Figure 4:
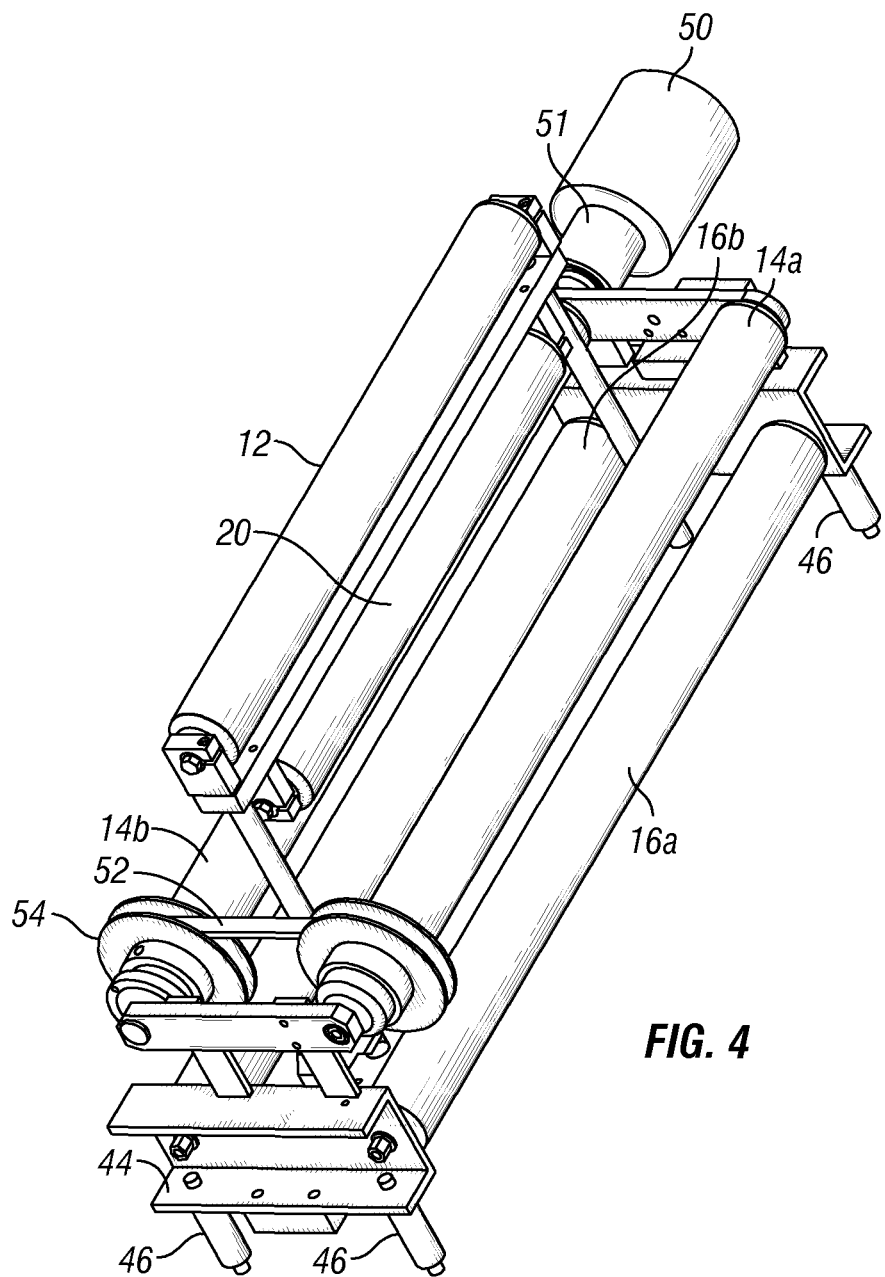
FIG. 4 is a perspective view of a tread inspection device in accordance with a particular embodiment of the invention.

With reference now to FIG. 4, a more particular embodiment of a tread inspection device 10 is shown. While the device shown includes the members discussed with regard to the embodiment shown in FIGS. 1-2, the device also shows a frame 44 to which the members 12, 14a, 14b, 16a, and 16b are operably attached. It is noted that frame 44 includes connection members 46 comprising pins to facilitate attachment of the device 10 to a tread support structure for retaining a length of the tread, or any other desired structure. For example, with reference to FIG. 5, device 10 is shown mounted to a tread support structure 60, where a portion of each pin 46 penetrates an aperture within the structure. It is contemplated that any manner of mounting, connecting, or attaching the device to a tread support structure may be employed to mount device 10 on any other structure as desired. In doing so, any component (which includes any member) of the device may be moveable relative other components so to increase the pathway opening to better receive the tread. In the embodiment shown, such movement facilitates separation between each of the opposing members 16a, 16b from the other members 14a, 14b for insertion of the tread into the device. The movement of any component may be accomplished by any known manner for achieving such movement. For example, any component, with or without a portion of the frame, may translate with any component and/or rotate or pivot to achieve such movement. By further example, any such movement may be achieved by any manual or mechanical device, such as a cylinder, motor, or drive. In the embodiment shown in FIG. 4, a drive source 50 is provided to drive either or both first and second members 14a, 14b and thereby translate the tread 30. The drive source 50 shown is a motor with a transmission 51 for selectively transmitting a drive force to the first and second members 14a, 14b. It is understood that any drive source known to one of ordinary skill for turning a roll or the like may be employed. It is also understood that the drive source may be automatic or manual. In is understood that any motor or drive with or without any known transmission member(s) known to one of ordinary skill may be employed, such as gears, belts, chains, or rack and pinion, for example. It is noted that a transmission member 52 extends between first and second members 14a, 14b, which allows the drive source to not only drive the second member 14b to which it is connected, but also to drive the first member 14a. In particular, the transmission member 52 comprises a belt are arranged within a groove of wheels 54, although any know transmission member or device may be employed known to one of ordinary skill to drive two or more rotatable members. In lieu of, or in addition to, a powered drive source, a manual drive source may be employed, such as a hand crank or the like, for selective operation of any first or second member 14a, 14b and/or to more precisely locate and inspect the tread.

It is noted that the inspection device may be mounted or secured to any other structure where tread inspection may occur. For example, with reference to the embodiment shown in FIG. 5, an inspection device 10 is adapted to be mounted to a tread support structure 60 comprising a roller table or conveyor table along which the tread is stored during inspection. The tread is able to be moved along the table by virtue of a plurality of rotatable members 62 arranged along a length of the table. Rotatable members 62 may comprise any rotatable member contemplated herein for rotatable members employed by device 10, including the rollers shown in the figure. The table includes an upper storage area 64 and a lower storage area 66 for the tread with a translation unit 68 extending there between to form a pathway for at least portions of the tread to translate between the top and bottom storage areas. Translation unit 68 may employ sliding surface and/or rotating members to facilitate translation of the tread between upper and lower storage areas 64, 66. It is understood that a cutting unit may also arranged along the table to cut lengths of tread as necessary. It is understood that any cutting device configured to cut treads or elastomeric material may be employed.

While this invention has been described with reference to particular embodiments thereof, it shall be understood that such description is by way of illustration and not by way of limitation. Accordingly, the scope and content of the invention are to be defined by the terms of the appended claims.

What is claimed is:

1. A method of inspecting a tread, the method comprising the steps of:
    providing a tread, comprising a demolded tread, having a length, a width, and a thickness bounded by a top side and a bottom side, one of the top and bottom sides including a tread feature extending into the thickness of the tread;
    bending mechanically a transverse extent of the tread relative the tread thickness along a portion of the tread to be inspected about a bending member to form a bent portion of the tread, the portion of the tread to be inspected including the tread feature where the tread feature to be inspected is arranged along a side of the tread opposite the bending member relative to the tread thickness such that the step of bending expands the tread feature to further expose a depth of the tread feature within the thickness of the tread for inspection such that the tread feature is expanded in a direction of the tread length;
    constraining the tread on opposing sides of the portion of the tread to be inspected to maintain the bent portion of the tread in a bent arrangement; and
    inspecting the tread feature arranged along the side of the tread opposite the bending member.

2. The method recited in claim 1 further comprising the step of:
    releasing the tread from constraint as achieved in the step of constraining;
    translating the tread relative the bending member to a second portion of the tread to be inspected, the second portion of the tread including a second tread feature extending into the thickness of the tread from one of the top and bottom sides; and,
    repeating the steps of bending and constraining in association with the second portion of the tread to be inspected.

3. The method recited in claim 2, where the tread is translated in the step of translating at a first speed or a second speed, the first speed being faster than the second speed to perform a fast transfer of the tread between the each portion of the tread to be inspected.

4. The method recited in claim 1 further comprising the step of:
    translating the tread relative the bending member after the bent portion of the tread has been inspected.

5. The method recited in claim 1, where the step of bending includes arranging the tread thickness to extend along a non-linear path extending between a first member and a second member and along the bending member located between the first and second constraining members along the path.

6. The method recited in claim 5, where the first member is a first constraining member and the second member is a second constraining member, and where the step of constraining the tread includes constraining the thickness of the tread at a first location with the first constraining member and at a second location with the second constraining member prior to the step of inspecting.

7. The method recited in claim 6, where each of the first and second constraining members are clamping members, and where the step of constraining the thickness of the tread at the first location and the second location is accomplished by clamping.

8. The method recited in claim 7, where the first constraining member operates in conjunction with a first opposing member arranged opposite the first constraining member relative the tread thickness to perform the step of constraining, and where the second constraining member operates in conjunction with a second opposing member arranged opposite the second constraining member relative the tread thickness to perform the step of constraining.

9. The method recited in claim 8, where each of the first and second constraining members and each of the first and second opposing members comprise a rotatable member having a rotatable axis about which an outer surface of the rotatable member rotates to engage the tread.

10. The method recited in claim 7, where each of the first and second constraining members operate in conjunction with a tread supporting structure to constrain the tread in the step of constraining, where the tread supporting structure supports portions of the tread separate from the portion being inspected.

11. The method recited in claim 10, where the tread supporting structure includes a plurality of rotatable members each having a rotatable axis about which an outer surface of the rotatable member rotates to facilitate translation of the tread along the tread supporting structure, where a first rotatable member of the plurality of rotatable members operates in conjunction with the first constraining member to constrain the tread in the step of constraining and a second rotatable member of the plurality of rotatable members operates in conjunction with the second constraining member to constrain the tread in the step of constraining.

12. The method recited in claim 6, where each of the first and second members comprise a rotatable member having a rotatable axis about which an outer surface of the rotatable member rotates to facilitate translation of the tread relative each of the first and second members.

13. The method recited in claim 9, where the rotational axis of each of the first and second members are arranged in parallel.

14. The method of recited in claim 9, where at least one of the first and second members are driven.

15. The method recited in claim 1, where the bending member extends longitudinally across at least a portion of a width or length of the tread.

16. The method recited in claim 1, where the bending member comprises a rotatable member having a rotatable axis about which an outer surface of the rotatable member rotates to facilitate translation of the tread relative the bending member.

17. The method recited in claim 16, where the bending member is moveable in a direction toward the first and second members and in a direction away from the first and second members.

18. An apparatus for inspecting a tread, the apparatus comprising:
   a pathway configured to receive a tread having a length defined by a first end and a second end each arranged on opposite ends of the tread length where the pathway receives the tread in a longitudinal direction arranging the first end and second end on opposite ends of the tread, comprising a demolded tread;
   a bending member configured to engage the tread arranged along the pathway where a tread feature to be inspected is arranged along a side of the tread strip opposite the bending member relative a tread strip thickness bounded by a top side and a bottom side;
   a first member arranged along the pathway;
   a second member arranged along the pathway, where the pathway extends lengthwise around a portion of the first member and around a portion of the bending member then around a portion of the second member, the bending member being arranged between the first and second members along the pathway; and
   a table,
   where the pathway extends from the table and to the first member and then from the second member and to the table, and
   where the table includes a lower storage area and an upper storage area, such that the pathway extends along each of the lower and upper storage areas.

19. The apparatus recited in claim 18, where each of the first and second members are constraining members.

20. The method of claim 1, where in the step of bending mechanically, where the length is defined by a first end of the tread and a second end of a tread and the first end of the tread is spaced apart from the second end of the tread.

21. The method of claim 20 further comprising a table, where the tread extends along the table.

22. The method of claim 21, where the table includes a lower storage area and an upper storage area, such that the tread extends along each of the lower and upper storage areas.

* * * * *